United States Patent [19]

Vallee et al.

[11] Patent Number: 5,087,759
[45] Date of Patent: Feb. 11, 1992

[54] SYNTHESIS OF VICINAL ALKANEDITHIOLS

[75] Inventors: Yannick Vallee, Caen; Yves Labat, Pau, both of France

[73] Assignee: Societe Nationale Elf Aquitaine (Production), Courbevoie, France

[21] Appl. No.: 476,244

[22] Filed: Feb. 7, 1990

[30] Foreign Application Priority Data

Feb. 8, 1989 [FR] France .................. 89 01635

[51] Int. Cl.$^5$ .................. C07C 149/06; C07C 148/00
[52] U.S. Cl. ...................................... 568/66
[58] Field of Search ............................. 568/66

[56] References Cited

U.S. PATENT DOCUMENTS 3,422,150 1/1969 Pflugfelder .................. 568/66

FOREIGN PATENT DOCUMENTS

CH-A443273 12/1965 France .
2102936 4/1972 France .................. 568/66

OTHER PUBLICATIONS

Taguchi, et al., Chemical Abstracts, vol. 72, 1970, Abstract 11980.
Speziale et al., Organic Synthesis Coll., vol. IV, 1963, pp. 401–403.
Iqbal et al., Chemical Abstracts, vol. 54, 1960, Abstract 16399 a–h.

Primary Examiner—Mukund J. Shah
Assistant Examiner—E. C. Ward
Attorney, Agent, or Firm—Morgan & Finnegan

[57] ABSTRACT

The invention relates to the manufacture of vicinal alkanedithiols from the corresponding alkylene trithiocarbonates.

The method according to the invention consists in treating alkylene trithiocarbonate with an alkaline sulfide, followed by acidification of the reaction medium.

The method is particularly well-suited for the synthesis of ethanedithiol from ethylene trithiocarbonate.

17 Claims, No Drawings

SYNTHESIS OF VICINAL ALKANEDITHIOLS

FIELD OF THE INVENTION

The present invention relates to the manufacture of vicinal alkanedithiols and, more particularly, the manufacture of ethanedithiol from ethylene trithiocarbonate.

BACKGROUND OF THE INVENTION

Ethanedithiol, $HS-CH_2CH_2-SH$, is an important mercaptan which has found various industrial uses, particularly as an intermediate in syntheses and as a vulcanization agent. It can be prepared by treating mercaptoethyl acetate with ammonium hydrosulfide at high temperatures and under pressure with hydrogen sulfide. See French Pat. No. 2,102,936. It can also be prepared from dibromethane by reaction with thiourea followed by potassium, hydroxide (*Organic Synthesis*, Coll., vol. IV, p. 401, (1963)). In addition, its synthesis is described in Belgian Patent No. 668,463 by the reaction of sodium trithiocarbonate with dichloroethane; however, under the conditions described, one obtains a mixture from which ethanedithiol is isolated with a yield of only 38%.

Older methods which permit the preparation of ethanedithiol from ethylene trithiocarbonate:

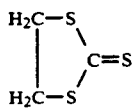

are described in the literature (cf. E. E. Reid, *Organic Chemistry of Bivalent Sulfur*, vol. I, Chemical Publishing, New York, pp. 41–42 (1958)). They consist in treating the ethylene trithiocarbonate with a base, a high temperature, and often under pressure. The yields of these reactions are in general very low and their reproducibility is low. Significant amounts, sometimes predominating amounts, of by-products are produced:

dimercaptoethyl sulfide: $HS-CH_2CH_2-S-CH_2CH_2-SH$ heavy oligomers and polymers of ethanedithiol.

T. Taguchi, et al., (*Tetrahedron Letters*, vol. 41, pp. 3631–3634, (1969)) have produced ethanedithiol by treating ethylene trithiocarbonate with ethanolamine at 80°–120 °C. In spite of its convenience, this method presents the drawback of producing a large amount of organic by-products which are difficult to recover. With regard to the methods involving the reduction of AlLiH$_4$ (S. M. Igbal, et al., *J. Chem. Soc.*, p. 1030 (1960)), their cost is prohibitive for industrial use.

The above references are hereby incorporated by reference.

DETAILED DESCRIPTION OF THE INVENTION

Ethylene trithiocarbonate is a product which is available readily; for example, it can be prepared quantitatively by reacting an alkaline trithiocarbonate with dichloroethane. It has now been discovered that ethylene trithiocarbonate can be advantageously converted into an ethanedithiol via a reaction with an alkaline sulfide, followed by a reaction with an acid according to the following reaction diagram:

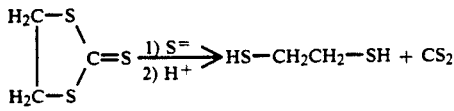

This method for the preparation of ethanedithiol can also be applied in general to the synthesis of vicinal alkanedithiols from the corresponding alkylene trithiocarbonate such as, for example, propylene trithiocarbonate which leads to 1,2-propanedithiol.

The method according to the invention is thus characterized in that it consists in reacting an alkylene trithiocarbonate with an alkaline sulfide in a solvent, followed by the acidification of the reaction medium and separation of the alkanedithiol formed.

The solvent used for the reaction of the alkylene trithiocarbonate with the alkaline sulfide can be water. However, better results are obtained, particularly a lower content of dimercaptoalkyl sulfide in the final crude product, by operating in a mixture of water and a water-soluble organic solvent such as, for example, a low-molecular-weight alcohol (1 to 4 carbon atoms), particularly methanol. It is possible to operate in the absence of water, for example in pure methanol; however, the results are not better. Preferably, one uses a volume ratio of water to alcohol between 90/10 and 10/90, and more particularly, between 50/50 and 25/75.

The solution of alkaline sulfide (for example $Na_2S$ or $K_2S$) can be obtained either by absorption of hydrogen sulfide in a solution of the corresponding alkaline hydroxide (NaOH or KOH), or by dissolution of a commercial solid sulfide (particularly $Na_2S$, $3H_2O$ or $Na_2S$, $9H_2O$) in the solvent. Although one can use very diluted solutions, it is economically more advantageous to operate with as concentrated as possible a solution of alkaline sulfide.

The temperature at which the reaction of the alkylene trithiocarbonate with the alkaline sulfide is conducted can vary within broad ranges. It can particularly range from room temperature to the reflux temperature of the solvent (64° C. in the case of methanol). However, it is preferable to operate at the reflux temperature; in that case on can use more concentrated solutions of alkaline sulfide (approximately 3.5 molar in comparison to 2 molar at room temperature) and thereby minimize the amount of solvent to be used. However, the present invention can operate at temperatures below room temperature, for example, with a nonhomogeneous mixture of solvent and alkaline sulfide, or under pressure at a temperature higher than the reflux temperature of the solvent at atmospheric pressure.

The amount of alkaline sulfide to be used can be between approximately one molar equivalent based on the alkylene trithiocarbonate and a large excess, for example three molar equivalents. However, it is preferable to operate with a slight excess of alkaline sulfide in comparison to the alkylene trithiocarbonate, for example from 1.05 to 1.6 equivalents. In this manner one achieves a nearly complete conversion.

The reaction can be run by mixing from the beginning the entire amount of alkylene trithiocarbonate with the alkaline sulfide. However, one achieves better results by adding the alkyline trithiocarbonate gradually into the solution of alkaline sulfide which is heated to reflux. For ethylene trithiocarbonate (m.p.=35° C.), it is more convenient to use it in the molten state, but solid ethylene trithiocarbonate can be used. The duration of the addition can vary within broad ranges as a function of the amounts used. It is usually between 5 and 120 minutes.

When the reaction is completed, which is reflected in a homogenization of the reaction medium, one proceeds then to the acidification of the reaction medium, preferably using a strong mineral acid such as, for example, hydrochloric acid or sulfuric acid. The amount of the acid to be used is at least the molar equivalent to the amount of alkaline cations ($Na^+$, $K^+$) used. To obtain a clearly acidic pH, it is advantageous to use a slight excess of acid, for example 1.1 equivalent $H^+$ per cation $Na^+$ or $K^+$. In addition, it has been observed that one obtains better yields when the reaction medium changes rapidly from a basic pH (pH>10) to a very acidic pH (pH=1-2). This abrupt change of pH can be obtained by mixing the acid and the reaction medium rapidly, or better by pouring the reaction medium into the acid.

After the acidification, an organic phase is decanted which contains alkanedithiol and carbon disulfide. The alkanedithiol can be separated readily from this phase, for example, by evaporation of $CS_2$, followed by distillation.

The method according to the invention permits the recycling of a part of the products used. The acidification of the reaction solution transforms the slight excess of alkaline sulfide used into hydrogen sulfide. The latter can then be recovered, for example by bubbling through a trap which contains an alkaline hydroxide, to reconstitute in this manner the starting alkaline sulfide. The carbon disulfide, which is produced by acidification and separated from the dithiol, can be reused for the synthesis of the starting alkylene trithiocarbonate. Finally, the solvent which can possibly be used can be separated from the water by distillation, preferably after the acidification. This distillation can possibly be conducted before the acidification, however, in that case one operates preferably under a slight vacuum to avoid unnecessary heating of the reaction products.

EXAMPLES

The following examples illustrate the invention without limiting it. The percentages indicated with respect to the VPC (Vapor phase chromatography) analyses take into account only the ethanedithiol, the dimercaptoethyl sulfide and the ethylene trithiocarbonate, and they are expressed on the basis of the total weight of the three compounds.

EXAMPLE 1

In 60 ml of water heated to reflux, and with stirring, one dissolves 14 g (0.1056 mol) $Na_2S$, $3H_2O$. Then one adds within 30 minutes 9 g (0.066 mol) ethylene trithiocarbonate. After completion of this addition, the mixture is maintained with stirring at reflux for an additional 45 minutes.

The reaction mixture is then acidified rapidly with 28 ml of 32% hydrochloric acid. The organic phase is decanted, and VPC analysis shows that it contains, in addition to carbon disulfide, 59% ethanedithiol, 36% dimercaptoethyl sulfide, and 5% ethylene trithiocarbonate.

By distillation, one recovers ethanedithiol with a yield of 48%.

EXAMPLE 2 (comparative)

2.8 g (0.0693 mol) of sodium hydroxide are dissolved in a mixture of 40 ml water and 80 ml methanol. The entire mixture is heated to reflux with stirring. Then one adds, within 30 minutes, 9 g (0.066 mol) of ethylene trithiocarbonate. After completion of the addition, the stirring at reflux is continued for an addition 10 minutes. Then the reaction mixture is acidified rapidly with 10 ml of 32% hydrochloric acid.

VPC analysis of the decanted organic phase shows that it contains, in addition to carbon disulfide, 30% ethanedithiol, 20% dimercaptoethyl sulfide, and 50% ethylene trithiocarbonate.

The ethanedithiol is recovered by distillation with a yield of 23%.

EXAMPLE 3

Into 20 ml of water and 40 ml of methanol, at reflux and with stirring, one dissolved 31.8 g (0.24 mol) $Na_2S$, $3H_2O$, followed by the addition within 40 minutes of 27 g (0.198 mol) of ethylene trithiocarbonate, and the stirring is continued for an additional 15 minutes after the end of the addition.

The reaction mixture is then acidified by pouring it into 60 ml of 32% hydrochloric acid. The organic phase is decanted, and VPC analysis shows that it contains, in addition to $CS_2$, 96% ethanedithiol, 2% dimercaptoethyl sulfide, and 2% ethylene trithiocarbonate.

14 g of ethanedithiol are recovered by distillation, equivalent to a yield of 75%.

EXAMPLE 4 a) Into a 5-liter reactor with a stirrer and thermostat, one charges 30 kg of an aqueous solution containing 70 moles $Na_2S$, and subsequently 6080 g (80 moles) carbon disulfide. After heating the mixture to the boiling temperature of the $CS_2$, the mixture is kept at this temperature for 3 hours. Then the excess $CS_2$ is eliminated by evaporation.

Subsequently, one introduces into the reaction medium, 6039 g (61 moles) dichloroethane in such a manner that the exothermal reaction can be controlled and the temperature of the medium does not exceed 80° C. This operation lasts approximately 3 hours. The organic phase is then decanted at approximately 40° C. It consists essentially of ethylene trithiocarbonate (8296 g).

b) Into the same reactor, one introduces a solution of 70 moles of $Na_2S$, $3H_2O$ in a mixture of 9760 g methanol and 5490 g water. Then the solution is heated to the boiling point of the methanol and the 8296 g of crude ethylene trithiocarbonate produced in the preceding step are introduced regularly within 1 hour. The reaction is continued for 2 hours with reflux, then the resulting homogeneous solution is removed from the reaction (solution 1).

c) Into the same reactor, one charges 30 kg of an aqueous solution with contains 144 moles of HCl. Then solution 1 is introduced regularly to control the exothermicity. The ethanedithiol and $CS_2$ which are formed are then separated from the aqueous phase by decanting. Subsequently the $CS_2$ can be separated readily from the crude ethanedithiol by evaporation under vacuum.

In this manner one obtains a produce whose weight composition, determined by VPC analysis, is as follows:
93% ethanedithiol,
5% dimercaptoethyl disulfide, 2% ethylene trithiocarbonate.

By distillation of this product, one obtained 4020 g of ethanedithiol with a purity higher than 99%, which corresponds to a yield of 70% based on the dichloroethane.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Method for the preparation of vicinal alkanedithiols, consisting of reacting an alkylene trithiocarbonate with an alkaline sulfide in a solvent, followed by acidification of the reaction medium and separation of the alkanedithiol produced.

2. Method according to claim 1, wherein the solvent is water or a water-soluble organic solvent.

3. Method according to claim 2, wherein the solvent is a alcohol containing 1 to 4 carbon atoms.

4. Method according to claim 1, wherein the solvent is a mixture of water and alcohol and with the volume ratio of water to alcohol being between 90/10 and 10/90.

5. Method according to claim 4, wherein the alcohol is methanol.

6. Method according to claim 4, wherein the volume ratio is between 50/50 and 25/75.

7. Method according to claim 2, wherein the reaction is conducted at a temperature ranging from room temperature to the reflux temperature of the solvent.

8. Method according to claim 7, wherein the reaction temperature is the reflux temperature of the solvent.

9. Method according to claim 1, wherein from 1 to 3 moles of alkaline sulfide per mole of alkylene trithiocarbonate is used.

10. Method according to claim 9, wherein from 1.05 to 1.6 moles of alkaline sulfide per mole of alkylene trithiocarbonate is used.

11. Method according to claim 1, wherein one uses sodium sulfide.

12. Method according to claim 7, wherein the alkylene trithiocarbonate is added gradually to the solution of alkaline sulfide.

13. Method according to claim 1, wherein the acidification is conducted with a mineral acid.

14. Method according to claim 13, wherein the mineral acid is hydrochloric acid.

15. Method according to claim 1, wherein the acidification is conducted by pouring the alkaline reaction medium into the acid.

16. Method according to claim 1, wherein the ethanedithiol is prepared from ethylene trithiocarbonate.

17. Method according to claim 1, wherein the 1,2-propanedithiol is prepared from propylene trithiocarbonate.

* * * * *